United States Patent
Kelemen et al.

(10) Patent No.: US 7,344,889 B2
(45) Date of Patent: Mar. 18, 2008

(54) CHEMICAL STRUCTURAL AND COMPOSITIONAL YIELDS MODEL FOR PREDICTING HYDROCARBON THERMOLYSIS PRODUCTS

(75) Inventors: Simon R. Kelemen, Annandale, NJ (US); Howard Freund, Neshanic Station, NJ (US); Michael Siskin, Randolph, NJ (US); David J. Curry, Katy, TX (US); Yitian Xiao, Sugar Land, TX (US); William N. Olmstead, Basking Ridge, NJ (US); Martin L. Gorbaty, Westfield, NJ (US); A. E. Bence, Friendswood, TX (US)

(73) Assignee: Exxonmobil Upstream Research Company, Houston, TX (US)

( * ) Notice: Subject to any disclaimer, the term of this patent is extended or adjusted under 35 U.S.C. 154(b) by 543 days.

(21) Appl. No.: 10/426,356

(22) Filed: Apr. 30, 2003

(65) Prior Publication Data

US 2004/0019437 A1 Jan. 29, 2004

Related U.S. Application Data

(60) Provisional application No. 60/376,897, filed on May 1, 2002.

(51) Int. Cl.
*G01N 33/24* (2006.01)
(52) U.S. Cl. .......................................... 436/29; 702/22
(58) Field of Classification Search ...................... None
See application file for complete search history.

(56) References Cited

U.S. PATENT DOCUMENTS

| | | | |
|---|---|---|---|
| 4,602,992 A | 7/1986 | Langhoff et al. | 208/412 |
| 4,624,776 A | 11/1986 | Long et al. | 208/302 |
| 5,774,381 A | 6/1998 | Meier | 364/578 |
| 6,013,172 A | 1/2000 | Chang et al. | 208/113 |

OTHER PUBLICATIONS

Wikipedia, Kerogen, http://en. wikipedia.org/wiki/Kerogen.*
Altgelt, K. H. and Boduszynski, M. M. (1994) *Composition and Analysis of Heavy Petroleum Fractions*, Marcel Dekker, New York, p. 64.
Faulon, J. L.; Carlson, G. A.; Hatcher, P. G., (1993) "Statistical Models for Bituminous Coal: A Three-Dimentional Evaluation of Structural and Physical Properties Based on Computer-Generated Structures". Energy and Fuels, vol. 7, pp. 1062-1072.
Faulon, J. L., (1994) "Stochastic Generator of Chemical Structure. 1. Application to the Structure Elucidation of Large Molecules". J. Chem. Inf. Sci. vol. 34, pp. 1204-1218.
Fletcher, Thomas H. and Kerstein, Alan R. (1992) "Chemical Percolation Model for Devolatilization. 3. Direct Use of$^{13}$C NMR Data to Predict Effects of Coal Type," American Chemical Society, *Energy & Fuels*, vol. 6, No. 4, pp. 414-431.
Freund, H. and Olmstead, W. N., (1989) "Detailed Chemical Kinetic Modeling of Butylbenzene Pyrolysis," *International Journ. of Chem. Kinetics*, vol. 21, pp. 561-574.
Kee, R. J.; Rupley, F. M.; and Miller, J. A. (1991) *"Chemkin-II: A Fortran Chemical Kinetics Package for the Analysis of Gas-Phase Chemical Kinetics,"* Sandia National Labs. SAND89-8009B.
Kelemen, S. R. et al. (1998) "Fuel, Lubricant and Additive Effects on Combustion Chamber Deposits", *Society of Automotive Engineers Technical Series*, Paper No. 982715.
Kowalewski, I.; Vandenbroucke, M.; Huc, A. Y.; Taylor, M. J.; Faulon, J. L., (1996) "Preliminary Results on Molecular Modeling of Asphaltenes Using Structure Elucidation Programs in Conjunction with Molecular Simulation Programs". Energy and Fuels, vol. 10 pp. 97-107.
Mae, K.; Maki, T.; Okutsu, H.; Miura, K., (2000) "Examination of Relationship Between Coal Structure and Pyrolysis Yields Using Oxidized Brown Coals Having Different Macromolecular Networks". Fuel, vol. 79, pp. 417-425.
Quann, R. J,; Jaffe, S. B., (1992) "Structure-Oriented Lumping: Describing the Chemistry of Complex Hydrocarbon Mixtures". I&EC Research, vol. 31, pp. 2483-2497.
Quann, R. J.; Jaffee, S. B., (1996) "Building Useful Models of Complex Reaction Systems in Petroleum Refining". Chemical Engineering Science, vol. 51, No. 10, pp. 1615-1635.
Ritter, Edward R. and Bozzelli, Joseph W. (1991) "THERM: Thermodynamic Property Estimation for Gas Phase Radicals and Molecules," *International Journ. of Chem. Kinetics*, vol. 23, pp. 767-778.

(Continued)

*Primary Examiner*—Yelena G. Gakh

(57) ABSTRACT

A method of predicting the composition of hydrocarbon products of a complex carbonaceous material when exposed to specific time and temperature conditions is disclosed. In one embodiment, the material is characterized to obtain elemental, chemical and structural parameters. A representative chemical structure of the material is constructed based on the characterization information. The representative chemical structure is then stochastically expanded to a molecular ensemble chemical structural model that includes heteroatoms. The chemical structural model is coupled to a compositional yield model and the composition of the material products is determined using kinetic modeling. Methods are provided of constructing a chemical structural model of complex carbonaceous material, of coupling a molecular ensemble of chemical structures to a thermal chemical mechanism, of updating an ensemble of chemical structures during the kinetic modeling to reflect chemical reaction products and of eliminating molecules from the system.

20 Claims, No Drawings

OTHER PUBLICATIONS

Savage, Phillip E. and Klein, Michael T. (1987) "Asphaltene Reaction Pathways—v. Chemical and Mathematical Modeling", *Chemical Engineering Science*, vol. 44, No. 2, pp. 393-404.

Serio, Michael A. et al. (1987) "Kinetics of Volatile Product Evolution in Coal Pyrolysis: Experiment and Theory", *Energy & Fuels*, vol. 1, pp. 138-152.

Solum, M. S. et al. (1989) "$^{13}$C Solid-State NMR of Argonne Premium Coals," *Energy & Fuels*, vol. 3, pp. 187-193.

Stull, D. R. and Prophet, H., editors (1971) *JANAF Thermochemical Tables*, National Bureau of Standards.

Takanohashi, T.; Kawashima, H., (2002) "Construction of a Model Structure for Upper Freeport Coal Using 13C NMR Chemical Shift Calculations". Energy and Fuels, vol. 16, pp. 379-387.

Tissot, B. P. and Welte, D. H. (1984) *Petroleum Formation and Occurrence*, 2$^{nd}$ Edition, Springer-Verlag, Berlin, p. 151.

Van Krevelen, D. W. (1983) *CRC Handbook of Solubility Parameters and Other Cohesion Parameters*, Barton, A. F. M. editor, CRC Press, Inc.; Boca Raton, p. 64.

Yoshida, T.; Sasaki, M.; Ikeda, K.; Mochizuki, M.; Nogami, Y.; Inokuchi, K., (2002) "Prediction of coal Liquefaction Reactivity by Solid State 13C NMR Spectra Data". Fuel, vol. 81, pp. 1533-1539.

Grant, D. M. et al. (1989) "Chemical Model of Coal Devolatilization Using Percolation Lattice Statistics", *Energy & Fuels*, v. 3, No. 2, pp. 175-186.

Meuzelaar, H. et al. (1987) "Prediction and Modeling of Coal Conversion Reactions by Pyrolysis Mass Spectrometry and Multivariate Statistical Analysis", *Fuel Processing Technology*, v. 15, pp. 59-70.

Neurock, M. et al. (1989) "Modeling Asphaltene Reaction Pathways: Intrinsic Chemistry", *AIChE Symposium Series*, v. 85, 273, pp. 7-14.

Niksa, S. (1991) "FLASHCHAIN Theory for Rapid Coal Devolatilization Kinetics. 1. Formulation", *Energy & Fuels*, v. 5, No. 5, pp. 647-665.

Squire, K. et al. (1986) "Tar Evolution from Coal and Model Polymers", *Fuel*, v. 65, No. 6, pp. 833-843.

Freund, Howard (1992) "Application of a Detailed Chemical Kinetic Model to Kerogen Maturation," *Energy & Fuels*, v. 6, pp. 318-326.

Ungerer, P. (1990) "State of the Art of Research in Kinetic Modeling of Oil Formation and Expulsion," *Advances in Organic Geochemistry*, v. 16, Nos. 1-3, pp. 1-25.

Ungerer, P. and Pelet, R. (1987) "Extrapolation of the Kinetics of Oil and Gas Formation from Laboratory Experiments to Sedimentary Basins," *Nature*, v. 327, pp. 52-54.

\* cited by examiner

CHEMICAL STRUCTURAL AND COMPOSITIONAL YIELDS MODEL FOR PREDICTING HYDROCARBON THERMOLYSIS PRODUCTS

This application claims the benefit of U.S. Provisional Application No. 60/376,897 filed May 1, 2002.

FIELD OF THE INVENTION

This invention relates generally to predicting the timing and composition of hydrocarbons generated from the thermal decomposition of complex carbonaceous materials, and the composition and structure of the materials and of the residue during and after generation.

BACKGROUND OF THE INVENTION

Complex, carbonaceous materials that are precursors for oil and gas can be found both in nature and in refining operations. One such material is kerogen. In geological terminology, kerogen is defined as organic matter, derived from plant and bacterial remains, dispersed in sedimentary rocks that is insoluble in traditional organic solvents. Kerogens yield hydrocarbons when the sediments undergo destructive distillation. Kerogens, and the sediments that contain them, can comprise what is known as hydrocarbon source rock. Predicting the timing and composition of hydrocarbon evolution from kerogens in source rocks under geological conditions is important for oil and gas exploration and exploitation. Coal, tar sands and bitumen are other examples of complex, carbonaceous materials occurring in nature. Complex, carbonaceous material is also found as a product in petroleum refining operations, know as residuum. Residua are those fractions that are non-distillable under given conditions and remain at the bottom of a distillation tower. Predicting the kinetics and product yields from the thermal decomposition of petroleum residua is important to refining operations e.g., coking processes.

Significant effort has been expended over the years to characterize kerogen from both chemical and physical perspectives. A common way to determine the composition of oil and gas produced from a given kerogen is to experimentally measure the kinetics and compositions of pyrolysis products and use that information to postulate the original chemical structure of the kerogen. During pyrolysis, a sample is rapidly heated, usually under exclusion of air, to a temperature high enough to break some of the chemical bonds. Knowledge of when and where bonds are formed and broken as well as how molecular structures change during a reaction is important in understanding the kinetics. Many laboratory experiments are needed to extract kinetic data and careful analysis of multiple types of analytical data is necessary to follow the compositional path of the generated hydrocarbons as they evolve. Furthermore, the results apply only to the particular kerogen being investigated.

One approach, as applied to coal, has been to use Fourier Transform Infrared spectroscopy ("FTIR") together with other techniques such as Thermal Gravimetric Analysis ("TGA"), Field Ionization Mass Spectroscopy ("FIMS") and Carbon13 Nuclear Magnetic Resonance spectroscopy ("NMR") to develop a chemical structural model of coal. Bond-breaking rules were developed to act on the chemical structural models of the coal to predict volatile organic matter evolution. A thermal-chemistry mechanism, used to describe the bond breaking processes, was simplified to about three to five steps. However, this type of model is not capable of predicting the timing and molecular composition of the hydrocarbon products at the level of detail required for hydrocarbon generation in nature or petroleum residua in refining operations because of oversimplification of either chemical structure representation or thermal-chemical mechanisms.

In the last decade, NMR and X-ray based solid state characterization techniques have progressed significantly toward quantifying average chemical structural properties of carbonaceous solids. Works have been published on the use of solid state $^{13}C$ NMR to determine parameters relating to carbon skeletal structure such as the average aromatic ring size and the number of attachments per aromatic cluster. X-ray Photoelectron Specrtroscopy (XPS) has been used to determine the functional forms of organic oxygen, sulfur and nitrogen and to determine the percentage of aromatic carbon. X-ray Absorption Near Edge Structure Spectroscopy (XANES) has been developed for sulfur speciation. The information from such direct characterization techniques has been combined to guide construction of chemical structural models for deposits formed in internal combustion engines.

Further, the pyrolysis of a generic asphaltene has been simulated by combining model-compound-deduced thermolysis kinetics and pathways with asphaltene chemical structure information. A stochastic approach, using a Monte Carlo simulation, was applied to the chemical structure information to construct an ensemble of thousands of chemical structures with particular reactive functionalities, where the ensemble average conformed with experimental observables. Such an ensemble has been connected to simple, but well-defined kinetic models. However, these models exclude heteroatoms and have been oversimplified in their development.

In order to extend NMR and X-ray based solid state characterization techniques used to quantify average chemical structural properties of complex carbonaceous materials toward a predictive compositional yields model, a method is needed to expand the average chemical structure to reflect the tremendous molecular diversity, including heteroatoms, within the material. It is this diversity that leads to the complex nature of crude oil and gas. A more realistic hydrocarbon compositional yield model capable of predicting the kinetics and composition of hydrocarbons generated from the thermal decomposition of complex carbonaceous materials, such as kerogen and petroleum residua, is also needed.

SUMMARY OF THE INVENTION

In one embodiment, a method of predicting the composition of hydrocarbon products of a complex carbonaceous material when exposed to specific time and temperature conditions is disclosed comprising: 1) characterizing the material to obtain elemental, chemical and structural parameters; 2) constructing a representative chemical structure of the material based on said characterization; 3) stochastically expanding the representative chemical structure to a molecular ensemble chemical structural model including heteroatoms; 4) coupling the chemical structural model to a compositional yield model; 5) determining the composition of the material products using kinetic modeling; and 6) updating the chemical structural model during the kinetic modeling to reflect chemical reaction products.

In another embodiment, a method of constructing a chemical structural model of a complex carbonaceous material is disclosed wherein the material is characterized to obtain elemental, chemical and structural parameters. A representative chemical structure of the material is then constructed based on the characterization and the representative chemical structure is stochastically expanded to a molecular ensemble chemical structure model such that heteroatoms are included.

In another embodiment, a method of coupling a molecular ensemble of chemical structures to a thermal-chemical mechanism is disclosed whereby a selected reactive functionality in the chemical structural model is related to a reaction step ascribed to that functionality in the thermal-chemical mechanism.

In yet another embodiment, a method of updating a molecular ensemble chemical structural model to reflect chemical changes that occur as a result of time and temperature conditions is disclosed. Selected reactive functionalities in the chemical structure model are characterized and chemical changes occurring to the selected reactive functionalities at specific time and temperature conditions are simulated with a kinetics model. The chemical changes are accounted for in the chemical structure model. The above steps are then repeated for at least one additional cycle.

In a further embodiment, a method of quantitatively determining removal of a molecule from a complex carbonaceous material as a result of chemical changes that occur at specified time and temperature conditions is disclosed. For geological time and temperature conditions, solubility parameters are compared for the material and the molecule. The molecule is eliminated when the molecule solubility parameter is sufficiently different from the solubility parameter of the material. For open system pyrolysis time and temperature conditions, boiling point or vapor pressure is compared to model the removal of the molecule from the complex carbonaceous material.

DETAILED DESCRIPTION OF THE INVENTION

To the extent that the following description is specific to a particular embodiment or a particular use of the invention, it is intended to be illustrative only, and is not to be construed as limiting the scope of the invention. On the contrary, it is intended to cover all alternatives, modifications, and equivalents that are included within the spirit and scope of the invention.

In one embodiment of the invention, a method of predicting the composition of hydrocarbon products of a complex carbonaceous material when exposed to specific time and temperature conditions is disclosed. The complex carbonaceous material is characterized to obtain elemental, chemical and structural parameters. A representative chemical structure of the material is then constructed based on the characterization and is stochastically expanded to a molecular ensemble chemical structural model including heteroatoms. The chemical structural model is coupled to a compositional yield model and the composition of the material products is determined using kinetic modeling. The chemical structural model is updated during the kinetic modeling to reflect chemical reaction products.

Detailed knowledge of the average chemical structure of complex carbonaceous materials is seen as a prerequisite for predicting the molecular composition of generated oil and/or gas as the material undergoes maturation or pyrolysis. In one embodiment, a method of initially constructing chemical structural ("CS") models of complex carbonaceous materials based on experimental data, but then expanded stochastically to a molecular ensemble, including heteroatoms, to reflect the tremendous molecular diversity within the material, is disclosed. In general, at least 10,000 cores are recommended as the basis for constructing a CS model. The term "core" as used herein means a contiguous ring system, and the term "corelink," simply means a link to a ring system, as illustrated in FIG. 1 below. The CS models are material-specific with the model input including, but not limited to, the elemental analysis and detailed solid state characterization of the complex carbonaceous material. Specifically, the CS model defines the set of reactive functionalities present in the complex carbonaceous material. The characterization data are converted into a chemical structure description of the complex carbonaceous material that is expanded stochastically using distribution functions to a large molecular ensemble on the order of about $10^6$ atoms. The distribution functions define the frequency of occurrence of a particular structural attribute, e.g., the frequency of occurrence of one aromatic ring structure is found in the aromatic ring size distribution function. The properties of the CS model, also called herein the "stochastic ensemble," are constrained so as to be consistent with the experimental results.

The terms "reactive functionality" and "functional group" are used interchangeably herein to mean a reactive local collection of atoms. In addition, the term "species" as used herein means molecules that contain a reactive functionality. A molecule can contain only one reactive functionality, although it can also contain a structural, non-reactive, functionality. Functional groups often include an atom other than carbon or hydrogen, such as sulfur, nitrogen and oxygen. These other atoms (i.e., not carbon or hydrogen) are called heteroatoms. In one embodiment, a method of coupling a thermal-chemical mechanism, referred to herein as a compositional yield model ("CYM") to the CS model (i.e., the stochastic ensemble) is disclosed. The CYM describes the bond breaking processes or "reaction steps" to form gas and/or liquid hydrocarbon products. To achieve coupling, selected species relate the ensemble of reactive functionalities in the CS model to a set of reaction steps ascribed to a particular functionality in the CYM. Hence, a mechanism is constructed consisting of species and the elementary steps involved in the chemistry of the particular reactive functionality. The elementary reaction steps in the CYM are numerically integrated for each time/temperature step. Most reaction steps can be determined by one skilled in the art from well-defined principles of thermal chemistry. The thermal chemistry of most molecular species can be determined by using the program THERM (Ritter, E. R. and Bozzelli, J. W., "*THERM: Thermodynamic Property Estimation for Gas Phase Radicals and Molecules,*" *Int. J. Chem. Kin.,* 23, 1991, pp. 767-778) and others (H, OH, H2O, CO2 etc.) can be assigned thermochemical parameters from the JANAF database (Stull, D. R. and Prophet, H., editors, *JANAF Thermochemical Tables*, National Bureau of Standards, 1971). Construction of the CYM and the determination of rate parameters rely on the wealth of fundamental knowledge available on elementary free-radical hydrocarbon reactions. Typical elementary reaction classes included in the CYM are initiation and termination, addition and β-scission, hydrogen transfer, and condensation reactions to allow for molecular weight growth (coke).

In another embodiment, a method of updating the CS model during kinetic modeling to reflect the chemical changes that occur as a result of the time/temperature history and reaction steps is disclosed. The model predicts product distributions from which aromaticity and ring size, H/C, boiling point distribution, heteroatom content and other properties can be readily determined. The model also quantitatively determines the products, both hydrocarbons and heteroatom containing compounds that are expelled from the complex carbonaceous material (i.e., eliminated from the system). Thus, the disclosed CS-CYM methodology leads to more accurate prediction of hydrocarbon yields for any time-temperature conditions of thermal stress.

Table 1 illustrates a list of the elemental, chemical and hydrocarbon skeletal parameters gathered on a particular kerogen (Type II). Kerogen Types I, II and III are used herein as defined in Tissot and Welte (Tissot, B. P. and Welte, D. H., *Petroleum Formation and Occurrence*, second edition, Springer-Verlag, Berlin, 1984, p. 151). These data, which can be gathered on any number of kerogens, or other complex carbonaceous material, are used to guide the development of a representative chemical structure prior to building a large (about $10^6$ atom) stochastic ensemble. These experimental observables constrain the choices of the structural features in each model. The first column in the table shows the experimental data, the next column represents the values from an average 100-300 atom CHO (carbon, hydrogen, oxygen) structure, that is the representative chemical structure shown in FIG. 1. The last column in the table contains the results from a CS model stochastic generation (including nitrogen and sulfur atoms). In general, there is good agreement between the elemental and chemical parameters.

In Table 1, hydrogen (H) and carbon (C) were determined from elemental analysis. The oxygen (O), sulfur (S) and nitrogen (N) were determined using XPS. The percent aromatic carbon is an average of the values determined by $^{13}C$ NMR and XPS. The percent naphthenic and aliphatic carbon were not determined experimentally, but were derived based on the CHO structure or the full stochastic CS model. The nitrogen and sulfur chemical types were determined by XPS and XANES respectively. The ratio MBCO/SBCO refers to the ratio of multiply-bound carbon oxygen to singly-bound carbon oxygen. This is an XPS parameter that is used to constrain the organic oxygen type. The multiply-bound carbon oxygen reactive functionalities are carbonyl and carboxyl while the singly-bound reactive functionalities are phenols, ethers and alcohols.

The carbon skeletal parameters were determined from Solid State $^{13}C$ NMR following the techniques developed by Solum et. al. (Solum, M. S., Pugmire, R. J., Grant, D. M., "$^{13}C$ *Solid-State NMR of Argonne Premium Coals,*" *Energy and Fuels*, 1989, 3, 187-193). The number of aromatic carbons per cluster is the average size of an aromatic. As used herein, a "cluster" represents a grouping of aromatic rings fused together. The percent of carbon as methyl groups (CH3) is determined by NMR. The NMR parameter of average aliphatic chain length reflects both the naphthene and alkyl carbon groups attached to an aromatic core. Following the technique of Kelemen et. al. (Kelemen, S. R., Siskin, M., Homan, H. S., Pugmire, R. J., Solum, M. S., "*Fuel, Lubricant and Additive Effects on Combustion Chamber Deposits,*" The Society of Automotive Engineers Technical Series Paper #982715, 1998), the NMR-derived parameter of the fraction of aromatic carbons with attachments ("FAA") indicates the extent to which the aromatic rings are substituted, including the attachment of naphthenic rings.

TABLE 1

TYPE II KEROGEN EXPERIMENTAL/MODEL PARAMETERS

| Parameters | Experimental | Basic CHO Structure | Stochastic Model |
|---|---|---|---|
| Elemental (Per 100 Carbons) | | | |
| Hydrogen | 117 | 118 | 119 |
| Oxygen | 9.7 | 8.5 | 9.6 |
| Sulfur | 1.4 | | 1.4 |
| Nitrogen | 2.9 | | 1.9 |
| Chemical | | | |
| % Aromatic (XPS/NMR) | 40 | 39 | 42 |
| % Alkyl | | 41 | 35 |
| % Naphthenic | | 17 | 20 |
| Mole % Nitrogen (XPS) Pyrrolic-Pyridinic-Other | 67-33-0 | | 66-34-0 |
| Mole % Sulfur (XANES/XPS) Aromatic - Aliphatic | 50-50 | | 49-51 |
| MBCO/SBCO | 1.1 | 1.0 | 1.2 |
| Skeletal | | | |
| Aromatic Carbons/Cluster | 12 | 14 | 12 |
| % Aliphatic $CH_3$ | 15.0 | 14.1 | 14.0 |
| Coordination Number | | 3.0 | 2.4 |
| Avg. Aliphatic Chain Length | 4.5 | 5.1 | 3.4 |
| Fraction of Aromatic Carbons with Attachments (FAA) | 0.43 | 0.39 | 0.46 |

FIGURE 1 - TYPE II KEROGEN CHO STRUCTURE
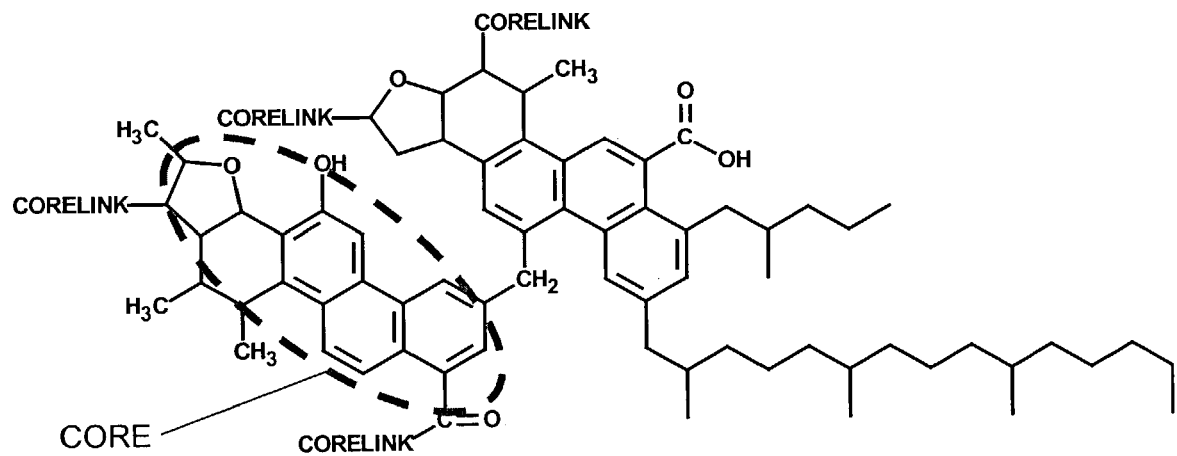

In one embodiment, distribution functions for particular chemical structure aspects of the complex, carbonaceous material are tracked during conversion of the entire ensemble. Distribution functions are configurations such as the: 1) number of aromatic rings per cluster; 2) number of naphthenic rings; 3) number of carbons in alkyl chains; 4) number of links per cluster; 5) oxygen, sulfur and nitrogen type distribution; and 6) the distribution of link type. These distribution functions can be estimated from available characterization data, such that the result is consistent with experimental observables. Often, distribution functions can be further constrained by the resulting bulk characterization of model parameters such as the hydrogen/carbon ratio (H/C) or the percent of aromatic carbon.

In one embodiment, a kerogen can be described in terms of aromatic and naphthenic ring systems with attached alkyl pendants and linked together with alkyl chains of varying lengths. Heteroatoms are added and the chemical nature of the links is tracked. Elemental analysis, in the form of O/C, S/C and N/C ratios, is obtained. The percent aromatic, naphthenic and alkyl carbon are also input. The naphthenic and alkyl carbon values are initially determined from a subjectively created carbon, hydrogen and oxygen (CHO) average molecular representation (e.g., two clusters of approximately one hundred atoms) that is consistent with the available elemental, $^{13}$C NMR chemical/lattice parameters, and XPS oxygen reactive functionality data. The amounts of the naphthenic and alkyl carbon can be adjusted from these initial values in the CS model to enhance agreement with all of the experimental parameters.

For the naphthenic distribution, an initial distribution can be estimated with the constraint being naphthenic ring systems no larger than five rings and total ring systems (naphthene plus aromatic) less than or equal to six.

The distribution function for the number of links per cluster also affects the overall H/C ratio of the system. In one embodiment, the CS model building method allows up to four links per cluster (in the kinetics module, this is increased to five to allow for condensation reactions). Typically, a very tight material that yields little liquid hydrocarbon would have mostly three and four links per cluster, whereas a much looser system, which liberates a substantial amount of hydrocarbon, might have two to three links per cluster.

For oxygen, one particular embodiment uses the reactive functionalities phenol, phenoxy (phenyl ether type), aromatic furan, naphthenic furan, carbonyl and carboxylic acid. The sum of the oxygen in the last two (the "multiply-bound carbon oxygen") divided by the oxygen in the first four yields the MBCO/SBCO parameter determined by XPS.

The distribution of sulfur species as aromatic and alkyl sulfur (thiophenic vs. sulfide) can be determined by Sulfur-XANES data. The nitrogen distribution used here contains only pyrrolic and pyridinic forms and can be determined by XPS data.

Attachment-type distribution refers to the location where reactive functionalities attach to a ring. Four kinds of attachments are described herein. Type 1 attachment is where the attachment is directly to the aromatic ring. Types 2 and 3 attachments refer to naphthenoaromatic links. A Type 2 attachment is next to the aromatic ring on the naphthene ring. The Type 3 attachment refers to an attachment to the non-benzylic carbon in a tetralin-like ring system. Type 4 attachment is a pure naphthenic attachment that is not next to an aromatic, although an aromatic could still be in the ring system. The aromatic part of the attachment distribution is quite sensitive to the fraction of aromatic carbons with attachments (FAA), which is a constraint imposed by solid state $^{13}$C NMR data. The Type 2 attachment is assumed to be more abundant than the Type 3 attachment because of favorable formation due to its more reactive benzylic nature. Specification of the attachment positions is needed because of their differences in thermal reactivity. This distribution function only applies to naphthenoaromatic structures since there is no ambiguity in link assignments for pure aromatics or pure naphthenes. Table 2 shows one example of the distribution functions used in stochastically constructing CS models for the Type II Kerogen shown in Table 1.

TABLE 2

EXAMPLE PARAMETER DISTRIBUTIONS FOR TYPE II KEROGEN (IN %)

| Aromatic Ring Size | |
|---|---|
| 0-Ring | 25 |
| 1-Ring | 45 |
| 2-Ring | 12 |
| 3-Ring | 6 |
| 4-Ring | 3 |
| 5-Ring | 3 |
| 6-Ring Plus | 6 |
| Alkyl Chains | |
| 1-Carbon | 66 |
| 2-5 Carbons | 21 |
| 6-14 Carbons | 11 |
| 15 Carbons Plus | 2 |
| Naphthenic Type | |
| Pure Naphthenic | 54 |
| Naphtheno-Aromatic | 46 |
| Links/Cluster | |
| 1 Link | 5 |
| 2 Links | 5 |
| 3 Links | 15 |
| 4 Links | 75 |
| Organic Sulfur | |
| Sulfidic | 45 |
| Thiophenic | 55 |
| Organic N | |
| Pyridinic | 25 |
| Pyrrolic | 75 |
| Organic Oxygen | |
| Phenol | 16 |
| Phenoxy | 14 |
| Furan | 30 |
| Carbonyl | 12 |
| Carboxyl | 28 |
| Link Type | |
| Aromatic | 25 |
| Naph-arom-1 | 20 |
| Naph-arom-2 | 10 |
| Naphthene | 45 |

Heteroatom functional groups can be added after the hydrocarbon framework has been created. Constraints can be imposed here to limit the number and type of heteroatoms in a given cluster.

Next, the attachment types can be distributed among the aromatic cores. Because phenoxy, sulfide and carbonyl can act as either links to other systems or be present in pendants, the attachment type is specified.

The final task of the CS model building process is to link up the clusters. One example of this is to use a moving window approach as each core is numerically linked to its neighboring cores (i.e., core #1 is attached to core #2 and depending on its specified number of links perhaps attached to cores #s 3, 4, and 5). Thus all of the cores are linked-up with each other to form a random macromolecular network. In one embodiment, a computer program can be used to keep track of specific attachments of each core.

With an initial ensemble constructed for the CS model, the chemical structural parameters can be examined for the closeness of fit to the available data. Input data can be slightly adjusted to enhance the agreement with the experimental characterization data. The H/C ratio and FAA are two of the experimental observables that may require adjustment of some of the input parameters for them to be matched. The number of links per cluster or the fraction of alkyl carbon vs. naphthenic carbon can be adjusted to bring the H/C ratio to the measured value. The FAA value can be determined after the CS model is created. It may be changed in the next iteration by changing the percentage of Type 1 links or the percentage of "zero" ring aromatics. The number of pure naphthenic rings affects FAA since naphthenoaromatic rings have at least two aromatic attachments while the naphthenes have zero. For those cases in which there are more than one naphthene on the aromatic system, the core can be represented by splitting the naphthenes and putting them on either side of the aromatic core or putting them on the same side of the aromatic core. The difference is that when they are split, there are twice the number of naphthenoaromatics or attachments onto aromatics. In one embodiment, the naphthenes are not split around the aromatic.

In all the structures, a nucleus of several cores can be identified that will ultimately become char during pyrolysis. These are the aromatic cores bound to other aromatic cores with a zero length link (biaryl linkages, e.g., biphenyl). No reaction step exists in the kinetics module to break zero length aromatic links, These connected cores are not eliminated or expelled from the CS model, at least in the high temperature mode, and can only grow. This feature of built-in coke make is determined primarily by the parameter that splits the alkyl carbon between links and pendants. Typically, the fraction of the alkyl carbon that is in links is 0.1 (10%). In construction of the CS model, when linking the clusters together, the available alkyl carbon will eventually be used up. All remaining links will then have zero length. By coupling a chemical mechanism of species to the CS model, and updating the CS model to reflect the bond breaking and chemistry which occurs in the mechanism, as the severity of pyrolysis increases, the CS model will involve aromatization, dealkylation, dehydrogenation/condensation (dimethylmethane to fluorene) and condensation reactions until it resembles coke or char.

With the CS model of the complex, carbonaceous material specified, the kinetics of its thermal decomposition and the yields of hydrocarbon products can be described. In one embodiment, thermal chemistry is used to describe kerogen transformation. Kerogen can be considered to be a set of reactive functionalities. An actual molecular reactive functionality, or species, that serves to relate the stochastic ensemble to a chemical reaction step is ascribed to each reactive functionality. It is these reaction steps that are numerically integrated under a given time/temperature step. The reactive functionalities can be assumed to be mobile and liquid-like so that liquid phase chemistry is applicable. In one example, nineteen different species are identified and tracked during the running of the kinetics program. Table 3 is a partial list of species showing their chemical designation.

TABLE 3

LIST OF SPECIES

| | |
|---|---|
| Alkylaromatic | (alkylaromatic or α-alkyltetralin linkage |
| β-naphtheno-aromatic | (β-alkyltetralin linkage) |
| γ-naphthenic | (alkyl-naphthenic linkage) |
| Naph-naphtheno-aromatic | |
| Naphtheno-aromatic | |
| Aromatic methyl | |
| Aromatic acid | |
| α-naphtheno-aromatic acid | |
| β-naphtheno-aromatic acid | |
| Naphthenic acid | |
| Phenol | |
| Bibenzyl initiator 1 | |
| Bibenzyl initiator 2 | |
| Bibenzyl initiator 3 | |
| Hetero-atom initiator 1 | |
| Hetero-atom initiator 2 | |
| Hetero-atom initiator 3 | |
| Large 4 ring + aromatic | (4 aromatic rings or more) |
| Naphthene | |

The first four listed in Table 3 are the dominant species needed to follow the primary carbon-carbon bond breaking that occurs in oil-bearing kerogen. The naphthene-naphthenoaromatic is a direct connection of a naphthenoaromatic to another naphthene or naphthenoaromatic species (link type 3 or 4). Naphtheno-aromatics are important species to track since they give up hydrogen as they aromatize. Hydrogen (H atom) is quite effective at removing aromatic methyl and OH. The acid reactive functionality was placed on four different positions available (aromatic, two on naphthenoaromatic and naphthenic).

Initiators have a bibenzyl-like character. The model considers initiators and the corresponding initiation reactions. For the heteroatom initiators, the bond between the aromatic heteroatom and either a benzyl functional group or an alkyl group can be considered a weak bond and hence is considered an initiator. Heteroatom initiators includes alkyl phenyl sulfides and alkyl phenyl ethers. The large (4 ring +) aromatic species is introduced to allow for condensation reactions, i.e., free radical addition into large aromatic structures.

The basic free-radical chemistry is rooted in the mechanism developed for butylbenzene as discussed in Freund, H. and Olmstead, W. N., "*Detailed Chemical Kinetic Modeling of Butylbenzene Pyrolysis,*" *Int. J. Chem. Kin.*, 21, 1989, pp. 561-574. Other alkyl containing reactants (β-alkyl tetralin and alkyl naphthenes) are added to that mechanism allowing for hydrogen transfer and β elimination at the ring. Naphthenoaromatic reactive functionalities are added, and these serve as a source for a stabilized benzylic radical. They can also aromatize and eliminate H atoms. For the acid reactive functionalities, hydrogen transfer from the acid yields a carboxyl radical that can readily split out $CO_2$. Water is primarily formed from OH, abstracting H with the OH coming from H attack on phenol. Additional water formation routes are the alcohol-acid esterification reaction between an acid and phenol and dehydrogenation of aliphatic alcohols. The alkyl carbonyl chemistry is simplified and represented by radical attack at an alkyl position beta to the carbonyl followed by elimination of CO.

The dominant radicals in the system are the resonantly stabilized reactive functionalities, such as benzyl, tetralyl, phenoxy, and the stabilized alkyl butylbenzyl radical. These reactive functionalities are much higher in concentration than other radicals and are expected to be the functional groups involved in addition reactions as well as at least one of the radicals in termination reactions. For addition, the tetralyl radical can add to either of the olefins, C*C or C*CC. The resulting radical can isomerize and then beta-eliminate the alkyl group leaving behind a dialin-like reactive functionality. This is the primary mode for olefin destruction along with H atom addition.

Two kinds of condensation reactions are considered: addition of a radical into a large aromatic and displacement of an aromatic methyl group. The radicals that can add to large aromatics are tetralyl, benzyl and phenoxy while benzyl and tetralyl are the radicals allowed to displace a methyl group.

Termination reactions are a special case. The termination reactions determine the overall rate and order of the decomposition. Termination reactions are the reverse of initiation and typically have no activation energy barrier. The dominant free radicals are assumed to be involved in termination. For termination to occur, one radical must react with another in a 2nd order reaction. However, because the radicals are present at very small concentrations, they will typically be quite far from one another. In a kerogen, they will not be able to readily "find" each other and hence cannot combine. To account for this in the model a factor is introduced based on structure that attenuates termination reactions. In one embodiment, the factor is based on the average molecular weight of the material $$F_1 = (MW)^{0.85}$$

In addition, a second factor $F_2$ is introduced which relates to the 'stiffness' of the material. This is the average length between links:

$$F_2 = exp((11-\text{linklength})/3)$$

Both of these factors ($F_1$ and $F_2$) attenuate recombination processes because of the lower collision probability between the two radicals. The recombination rate constant is thus divided by $F_1$ and $F_2$.

In general, all radical reactions are reversible with the reverse rate constant being determined by the forward rate constant and the equilibrium constant for the reaction. This equilibrium constant is determined by the thermochemistry of the species involved. Thermochemistry of most species is determined by the program THERM although some of the smaller species (H, OH, H2O, CO2 etc.) are assigned thermodynamic parameters from the JANAF database.

For example, consider 147 total species considered of which 92 are "stable," molecular species and 55 free radicals. Any number of species could be chosen and this number was selected for illustration purposes only. The number of reactions totals 443. These are partitioned in the following way: 65.9% H transfer, 0.9% ipso H attack, 1.8% isomerization, 5.2% acid chemistry, 18.1% addition/beta-elimination, 4.1% reactions associated with condensation and 14% initiation/termination. Rate parameters are typically derived from literature values. Some of the condensation reaction kinetic parameters are freely varied.

In one embodiment, the CYM is coupled to the CS model (stochastic ensemble) through the selected species. The reactive functionalities are counted in the ensemble, normalized and then sent as a mole fraction to a kinetics model. The kinetics model is turned on for a short time (i.e., the chemical mechanism is numerically integrated) and reactions are allowed to occur at a given time and temperature. Any conversion is accounted for in the CS model, and then the reactive functionalities are counted up again, normalized and sent back to the kinetics module. This accounting routine looks at the selected reactive functionalities and the products produced from them. Based on the changes observed in these reactive functionalities as the CYM is integrated over the time/temperature interval, similar changes are made in the ensemble to reflect the reactions.

Concentration of the total reactive functionalities in the kerogen is assumed constant as a function of temperature/conversion (i.e., little change in bulk density with temperature). The initial concentrations are determined from the ensemble. The number present in the ensemble of the largest reactive functionality (e.g. alkylaromatic for a Type I kerogen) is divided by the total mass of the ensemble to yield a molar concentration for this particular functionality. The molar concentration is converted to a gas phase equivalent pressure at 300K assuming ideal gas law. A gas phase model, such as described in Kee, R. J.; Rupley, F. M.; and Miller, J. A.; "Chemkin-II: A Fortran Chemical Kinetics Package for the Analysis of Gas-phase Chemical Kinetics"; SAND89-8009B; Sandia National Laboratories, 1991, can be used as the kinetics model. The initial total pressure that would represent the kerogen is determined by dividing this pressure by the mole fraction of the given reactive functionality as determined from the stochastic ensemble. In order to avoid having initial pressure be a function of the starting material, a total initial pressure is specified.

In one example, the kinetic model was initially tuned to non-isothermal, open system laboratory data. The kerogen was heated, eventually decomposed and the products continually removed from the system, either by inert gas flow or by a vacuum pump. A "reactor cut-point" of about 1250° F. was determined for typical open system pyrolysis reactors used in geochemical applications. This means that a molecule generated by the kerogen with an atmospheric boiling point above 1250° F. would stay in the reactor while a molecule with a lower boiling point would be swept out. This aspect was incorporated into the kinetic model for open system laboratory pyrolysis. The boiling point of a given molecule can be determined using crude oil correlations developed by Altgelt and Boduszynski (see Altgelt, K. H. and Boduszynski, M. M., *Composition and Analysis of Heavy Petroleum Fractions*, Marcel Dekker, New York, 1994, p. 64). It requires that the H/C ratio and molecular weight of the molecule be known. The correlation used for NBP>500° F. was $$NBP(° F.) = [(MW - 170)/(2.67E-7)(H/C)^{0.9}]^{0.3333}$$

Hence, by knowing the molecular weight (MW) and H/C ratio of a product molecule generated by the CYM program, it can be determined whether it would remain in the reactor (of a specified cut point) for possible further reaction or be swept out.

In a further embodiment, a method of quantitatively determining removal of a molecule from a complex carbonaceous material as a result of chemical changes that occur at specified time and temperature conditions is disclosed. For geological conditions, a method is disclosed whereby solubility parameters are determined for the bulk kerogen as well as the molecule in question. Solubility parameters can be estimated using a group additivity approach as described in Van Krevelen, D. W. in *CRC Handbook of Solubility Parameters and Other Cohesion Parameters*, Barton, A. F. M. editor; CRC Press Inc.; Boca Raton, 1983, p. 64. The criterion for expulsion, i.e., elimination from the system, is based upon the solubility parameter of the product molecule of the kerogen. If the solubility parameter of a given molecule is sufficiently less than the solubility parameter of the kerogen, that molecule will be removed from the system and considered product. The probability of removal of the molecule increases as the difference between the molecule and material parameter increases. If the solubility parameter is not small enough, the molecule will remain with the kerogen for further reaction. One skilled in the art may set the degree of difference as a design criteria for a particular model. For open system pyrolysis time and temperature conditions, the parameters of boiling point or vapor pressure can be compared to model the removal of the molecule from the complex carbonaceous material.

Tables 4 and 5 illustrate CS-CYM output for the Type II Kerogen shown in Table 1. Under the geological heating rate, the $C_{15}^+$ NSO decimal mass fraction of Hydrogen Index (HI) is less than under the laboratory heating rate while the $C_{15}^+$ Saturates/Aromatics decimal mass fraction of HI is greater. The CS-CYM kinetic results for the Type II kerogen shown in Table 1 are pre-exponential of 1.20E+12 ($sec^{-1}$) and activation energy of 46.3 (kcal/mole). The temperature for the maximum rate of hydrocarbon generation under a geological heating rate is 298° C. lower than at the laboratory heating rate.

TABLE 4

CS-CYM YIELDS FOR TYPE II KEROGEN

| | Decimal Mass Fraction of HI | | | | |
|---|---|---|---|---|---|
| | Methane | $C_2$-$C_5$ | $C_6$-$C_{14}$ | $C_{15}+$ Sat/Arom | $C_{15}+$ NSOs |
| Laboratory Heating Rate (3° C./min) | 0.03 | 0.08 | 0.22 | 0.30 | 0.37 |
| Geological Heating Rate (3° C./10⁶ Years) | 0.02 | 0.11 | 0.38 | 0.45 | 0.04 |

TABLE 5

CS-CYM RESULTS FOR TYPE II KEROGEN

| | Hydrogen Index (mg/g) | Tmax (° C.) | Char (wt %) | H/C Char |
|---|---|---|---|---|
| Laboratory Heating Rate (3° C./min) | 554 | 415 | 48 | 0.55 |
| Geological Heating Rate (3° C./10⁶ Years) | 489 | 117 | 53 | 0.58 |

Table 6 shows the results of open system pyrolysis experiments on Type II Kerogen compared to the CS-CYM results. The experiments and model were run at 25° C./min up to 600° C. The $C_1$-$C_5$, $C_6$-$C_{14}$ and $C_{15}^+$ data are expressed as a decimal mass fraction of the Hydrogen Index (HI). The weight percent char is based on the amount of starting kerogen.

TABLE 6

PYROLYSIS RESULTS OF TYPE II KEROGEN

| | Decimal Mass Fraction of HI | | | | |
|---|---|---|---|---|---|
| | HI (mg/g) | $C_1$-$C_5$ | $C_6$-$C_{14}$ | $C_{15}^+$ | Weight % Char |
| CS-CYM Output | 558 | 0.12 | 0.16 | 0.72 | 47.4 |
| Experimental Result | 532 | 0.10 | 0.12 | 0.78 | 49.1 |

The foregoing description, including any discussions of chemical theory, has been directed to particular embodiments of the invention for the purpose of illustrating the invention, and is not to be construed as limiting the scope of the invention. It will be apparent to persons skilled in the art that many modifications and variations not specifically mentioned in the forgoing description will be equivalent in function for the purposes of this invention. All such modifications, variations, alternatives, and equivalents are intended to be within the spirit and scope of the present invention, as defined by the appended claims.

What is claimed is:

1. A computer-implemented method of predicting the timing and composition of hydrocarbon products of thermal decomposition of a complex carbonaceous material when exposed to a specified time and temperature history having starting and ending points, comprising:

a) characterizing the material to obtain elemental, chemical and structural parameters, said elemental parameters representing relative concentrations of selected chemical elements including heteroatoms occurring in the complex carbonaceous material, said chemical parameters representing relative abundance of selected chemical bonds occurring in the complex carbonaceous material, and said structural parameters being representative of the skeletal structure in which atoms are arranged in the complex carbonaceous material;

b) constructing a representative chemical structure of the material based on said characterization, said representative chemical structure including at least carbon, hydrogen and oxygen atoms;

c) inputting said representative chemical structure into a computer and stochastically expanding the representative chemical structure to a molecular ensemble chemical structural model including heteroatoms;

d) coupling the chemical structural model to a compositional yield model having kinetic modeling capability, i.e. a compositional yield model comprising species and elementary reaction steps involved in the chemistry of reactive functionalities present in the complex carbonaceous material;

e) selecting a time and temperature step at said starting point;

f) determining the composition and quantity of said hydrocarbon products of thermal decomposition for the selected time and temperature step using kinetic modeling;

g) updating the chemical structural model during the kinetic modeling to reflect chemical reaction products;

h) identifying any chemical reaction products that are removed from the updated chemical structural model of the complex carbonaceous material, said removed products being said hydrocarbon products of thermal decomposition;

i) incrementally advancing the time and temperature step and repeating steps (f)-(i) until the time and temperature history end point has been reached.

2. The method of claim 1 wherein said material is characterized in the solid state by elemental analysis and by additional methods comprising a plurality of methods selected from the group consisting of X-ray photoelectron spectroscopy (XPS) analysis, solid state nuclear magnetic resonance (NMR), and X-ray absorption near edge structure spectroscopy (XANES).

3. The method of claim 1 wherein said representative chemical structure contains a number of atoms ranging from about one hundred to about three hundred atoms.

4. The method of claim 1 wherein the representative chemical structure is stochastically expanded using distribution functions such that the properties of the molecular ensemble chemical structural model are consistent with the characterization.

5. The method of claim 1 wherein said complex carbonaceous material is kerogen.

6. The method of claim 1 wherein said complex carbonaceous material is petroleum residuum.

7. The method of claim 1 wherein said molecular ensemble is on the order of about $10^6$ atoms.

8. The method of claim 1 wherein said material characterization includes carbon, hydrogen, oxygen, nitrogen, sulfur, aromatic carbon, alkyl carbon, and naphthenic carbon.

9. The method of claim 1 wherein the coupling of the structural model to a compositional yield model comprises relating a selected reactive functionality in said structural model to a reaction step ascribed to said functionality in said compositional yield model.

10. The method of claim 1 wherein updating the chemical structural model comprises:
    a) characterizing selected reactive functionalities in said chemical structural model;
    b) simulating chemical changes occurring to said selected reactive functionalities at current time and temperature conditions with the kinetics model;
    c) accounting for said chemical changes in the chemical structural model;
    d) repeating steps (a) through (c) for at least one additional cycle.

11. The method of claim 10 wherein said characterizing selected reactive functionalities comprises counting and normalizing said selected reactive functionalities.

12. The method of claim 11 wherein a mole fraction is calculated from the results of said counting and normalizing for input into said kinetics model.

13. The method of claim 1 wherein determining whether a chemical reaction product will be removed from the updated chemical structural model of the complex carbonaceous material comprises:
    a) determining and comparing a molecular parameter of said chemical reaction product with the same parameter of said updated chemical structural model of the complex carbonaceous material;
    b) removing said chemical reaction product when the molecule parameter differs from the material parameter by more than a pre-set amount.

14. The method of claim 13 wherein said specified time and temperature history is geological time and temperature history and said parameter is solubility.

15. The method of claim 14 wherein the solubility parameter is estimated using a group additivity approach.

16. The method of claim 13 wherein said specified time and temperature history is open system pyrolysis time and temperature history and said parameter is selected from the group consisting of boiling point and vapor pressure.

17. The method of claim 1, wherein the chemical elements selected for the elemental parameters include at least hydrogen, oxygen, sulfur and nitrogen, and their relative concentrations are expressed relative to carbon concentration in the form of H/C, O/C, S/C and N/C ratios, said ratios being determined by elemental analysis.

18. The method of claim 1, wherein said chemical parameters are in the form of at least mole percent aromatic carbon, alkyl carbon, naphthenic carbon, and methyl carbon, mole percent aromatic sulfur and aliphatic sulfur, mole percent pyrrolic nitrogen and pyridinic nitrogen and mole percent of multiply-bonded carbon oxygen species (carbonyl plus carboxyl) and singly-bound carbon oxygen species (phenols, ethers and alcohols).

19. The method of claim 1, wherein said structural parameters are parameters of the skeletal core structure in the form of at least average aromatic carbons per aromatic core, average aliphatic carbon chain length and fraction of aromatic carbons with attachments.

20. The method of claim 1, wherein all elemental, chemical and structural parameters are determined from experimental data except percent naphthenic carbon and percent alkyl carbon which are initially derived based on the representative chemical structure of the complex carbonaceous material or the stochastic expansion of the representative chemical structure.

* * * * *